(12) United States Patent
Yin et al.

(10) Patent No.: US 9,451,768 B2
(45) Date of Patent: Sep. 27, 2016

(54) BIOCIDAL COMPOSITIONS AND METHODS OF USE

(75) Inventors: Bei Yin, Buffalo Grove, IL (US); Michael V. Enzien, Lisle, IL (US); Donald J. Love, Midland, MI (US)

(73) Assignee: Dow Global Technologies LLC, Midland, WI (US)

( * ) Notice: Subject to any disclaimer, the term of this patent is extended or adjusted under 35 U.S.C. 154(b) by 729 days.

(21) Appl. No.: 12/818,581

(22) Filed: Jun. 18, 2010

(65) Prior Publication Data

US 2011/0108493 A1    May 12, 2011

Related U.S. Application Data

(60) Provisional application No. 61/259,800, filed on Nov. 10, 2009.

(51) Int. Cl.
*A01N 37/34* (2006.01)
*A01N 43/90* (2006.01)

(52) U.S. Cl.
CPC ............... *A01N 37/34* (2013.01); *A01N 43/90* (2013.01)

(58) Field of Classification Search
CPC ............................ A01N 43/90; A01N 37/34
USPC ........................................ 514/246, 528, 727
See application file for complete search history.

(56) References Cited

U.S. PATENT DOCUMENTS

| 3,981,998 | A |   | 9/1976  | Waldstein |         |
|-----------|---|---|---------|-----------|---------|
| 4,163,795 | A |   | 8/1979  | Burk      |         |
| 4,732,913 | A | * | 3/1988  | Donofrio et al. | 514/528 |
| 4,978,512 | A |   | 12/1990 | Dillon    |         |
| 5,016,714 | A |   | 5/1991  | McCabe et al. |    |
| 5,347,007 | A |   | 9/1994  | Das et al. |        |
| 5,637,587 | A | * | 6/1997  | Gross et al. | 514/244 |
| 8,222,250 | B2 |  | 7/2012  | Annis et al. |       |
| 2007/0251889 | A1 | * | 11/2007 | Singleton et al. | 210/764 |
| 2008/0004189 | A1 |   | 1/2008  | Smith et al. |   |
| 2009/0325965 | A1 | * | 12/2009 | Annis et al. | 514/244 |

FOREIGN PATENT DOCUMENTS

| CN | 102076217 A | 5/2011 |
| JP | 2000119111 A | 4/2000 |
| WO | 2009015088 | 1/2009 |
| WO | 2009039004 | 3/2009 |

OTHER PUBLICATIONS

Block, S.S. Disinfection, Sterilization, and Preservation. 4th ed., Lea & Febiger, Philadelphia, 1991, pp. 305-306.*
De Groot et al., "Formaldehyde-releasers: relationship to formaldehyde contact allergy. Contact allergy to formaldehyde and inventory of formaldehyde-releasers", Contact Dermatitis, 2009, vol. 61, pp. 63-85.
Shao et al., "Mechanism of Chrome-free Tanning with Tetra-Hydroxymethyl Phosphonium Chloride", Chinese Journal of Chemical Engineering, Chemical Industry Press, 2008, vol. 16 No. 3, pp. 446-450.
Databse WPI Week 199705 Thomson Scientific, London, GB; AN 1997-048200 XP002599368 & JP 8301708 Abstract.
United States Environmental Protection Agency: "Reregistration Eligibility Decision (RED)—Methylene bis (thiocyanate)" Office of Prevention, pesticides and toxic substances XP007914718.
International Search Report and Written Opinion for PCT/US2010/039153 dated Oct. 27, 2010.

* cited by examiner

*Primary Examiner* — John Pak
(74) *Attorney, Agent, or Firm* — Tifani M. Edwards

(57) ABSTRACT

Provided are biocidal compositions comprising 2,2-dibromo-3-nitrilopropionamide and a compound selected from the group consisting of 1-(3-chloroallyl)-3,5,7-triaza-1-azoniaadamantane; tris(hydroxymethyl)-nitromethane; and a hexahydrotriazine compound. The compositions are useful for controlling microorganisms in aqueous or water containing systems.

8 Claims, No Drawings

BIOCIDAL COMPOSITIONS AND METHODS OF USE

CROSS-REFERENCE TO RELATED APPLICATIONS

This application claims the benefit of U.S. Provisional Application Ser. No. 61/259,800, filed Nov. 10, 2009, which is incorporated herein by reference in its entirety.

FIELD OF THE INVENTION

The invention relates to biocidal compositions and methods of their use for the control of microorganisms in aqueous and water containing systems. The compositions comprise 2,2-dibromo-3-nitrilopropionamide together with a second biocide.

BACKGROUND OF THE INVENTION

Protecting water-containing systems from microbial contamination is critical to the success of many industrial production processes, including oil or natural gas production operations. In oil and gas production, microorganism contamination from both aerobic and anaerobic bacteria can cause serious problems such as reservoir souring (mainly caused by anaerobic sulfate-reducing bacteria (SRB)), microbiologically influenced corrosion (MIC) on metal surfaces of equipment and pipelines, and degradation of polymer additives.

Microbial contamination can occur anywhere throughout oil and gas operations including injection water, produced water, downhole, near wellbore areas, deaeration towers, transmission pipelines, source water for waterflooding and hydraulic fracturing such as pond water and holding tank water, oil and gas storage tanks, and functional water-based fluids such as drilling muds, completion or workover fluids, hydrotest fluids, stimulation fluids, packer fluids, and fracturing fluids.

Biocides are commonly used to disinfect and control the growth of microorganisms in aqueous systems. However, not all biocides are effective against a wide range of microorganisms and/or temperatures, and some are incompatible with other chemical treatment additives. In addition, some biocides do not provide microbial control over long enough time periods. In oil and gas applications, the presence of $H_2S$ and high temperature (up to 120° C. or higher) present significant and unique challenges for biocide treatments.

2,2-dibromo-3-nitrilopropionamide (DBNPA) is an effective fast-acting biocide used in many industrial processes including oil and gas operations. It is also known, however, that DBNPA readily undergoes hydrolytic degradation that is accelerated with high pH or temperature. DBNPA, therefore, generally cannot provide long-lasting microbial control. As a result, it would be a significant advance in the field to provide biocides that can control a wide range of microorganisms and are both fast-acting and long-lasting.

BRIEF SUMMARY OF THE INVENTION

In one aspect, the invention provides biocidal compositions. The compositions are useful for controlling microbial growth in aqueous or water-containing systems. The compositions of the invention comprise 2,2-dibromo-3-nitrilopropionamide together with a biocidal compound selected from the group consisting of 1-(3-chloroallyl)-3,5,7-triaza-1-azoniaadamantane; tris(hydroxymethyl)-nitromethane; and a hexahydrotriazine compound.

In a second aspect, the invention provides a method for controlling microorganisms in aqueous or water containing systems. The method comprises treating the system with an effective amount of a biocidal composition as described herein.

DETAILED DESCRIPTION OF THE INVENTION

As noted above, the invention provides biocidal compositions and methods of using them in the control of microorganisms. The compositions comprise 2,2-dibromo-3-nitrilopropionamide (DBNPA) together with a biocidal compound selected from the group consisting of: 1-(3-chloroallyl)-3,5,7-triaza-1-azoniaadamantane; tris(hydroxymethyl)-nitromethane; and a hexahydrotriazine compound. It has surprisingly been discovered that combinations of DBNPA with other biocidal compounds as described herein are synergistic when used for microorganism control in aqueous or water containing media. That is, the combined materials result in improved biocidal properties than would otherwise be expected based on their individual performance at the particular use-concentration. The observed synergy permits reduced amounts of the materials to be used to achieve acceptable biocidal properties, thus potentially reducing environmental impact and materials cost.

In addition to exhibiting synergy, the compositions of the invention are also effective for controlling a wide range of microorganism types, including both aerobic and anaerobic microorganisms. Further, the compositions are functional for extended time periods and under conditions typically found in oil and gas applications. As a result of these attributes, the compositions are particularly useful in the oil and natural gas industry where biocidal agents are needed that are capable of controlling both aerobic and anaerobic bacteria, and providing both rapid decontamination and extended protection.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation.

In a first embodiment, the composition of the invention comprises: 2,2-dibromo-3-nitrilopropionamide ("DBNPA") and 1-(3-chloroallyl)-3,5,7-triaza-1-azoniaadamantane ("CTAC"). The CTAC compound may be the cis isomer, the trans isomer, or a mixture of cis and trans isomers. Preferably, it is the cis isomer or a mixture of the cis and trans isomers.

Preferably, the DBNPA to CTAC weight ratio in the first embodiment of the invention is about 100:1 to 1:100, more preferably 50:1 to 1:50, and even more preferably 35:1 to 1:35. In a particularly preferred embodiment, the DBNPA to CTAC weight ratio is between about 10:1 to 1:34.

In a further embodiment, the DBNPA/CTAC composition further comprises 2-bromo-2-nitropropane-1,3-diol ("Bronopol" or "BNPD") as a third biocidal compound. Preferably, the DBNPA to bronopol weight ratio in this embodiment is between about 1:1 and 1:5 and the bronopol to CTAC weight ratio is between about 1:2 and about 1:8.

In a further embodiment, the microorganism is aerobic. Under this embodiment, a preferred DBNPA to CTAC weight ratio is between about 10:1 to 1:34.

In a yet a further embodiment, the microorganism is anaerobic. Under this embodiment, a preferred DBNPA to CTAC weight ratio is between about 9:1 to 1:3.

In a still further embodiment, the microorganism is anaerobic and sulfide ion is present in the aqueous system to be treated. Under this embodiment, the DBNPA to CTAC weight ratio is preferably between about 2:1 to 1:8.

DBNPA and CTAC are commercially available from The Dow Chemical Company and/or can be readily prepared by those skilled in the art using well known techniques.

In a second embodiment, the composition of the invention comprises DBNPA and tris(hydroxymethyl)nitromethane ("tris nitro"). Preferably, the DBNPA to tris(hydroxymethyl)nitromethane weight ratio in this second embodiment is between about 100:1 to 1:100, more preferably 50:1 to 1:50, and even more preferably 20:1 to 1:20. In a particularly preferred embodiment, the DBNPA to tris(hydroxymethyl)nitromethane weight ratio is between about 9:1 to 1:8.

In a further embodiment, the microorganism is aerobic. Under this embodiment, a preferred DBNPA to tris nitro weight ratio is between about 1:3 to 1:8.

In a yet further embodiment, the microorganism is anaerobic. Under this embodiment, the DBNPA to tris nitro weight ratio is preferably about 9:1.

Tris(hydroxymethyl)nitromethane is commercially available from The Dow Chemical Company and/or can be readily prepared by those skilled in the art using well known techniques.

In a third embodiment, the composition of the invention comprises 2,2-dibromo-3-nitrilopropionamide and a hexahydrotriazine compound. Preferably, the hexahydrotriazine compound is of the formula I:

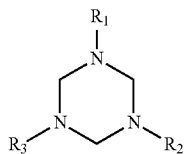

I wherein $R_1$, $R_2$, and $R_3$ are independently selected from the group consisting of hydrogen, $C_1$-$C_5$ alkyl, $C_1$-$C_5$ hydroxyalkyl, or an alkoxyalkylene group having the structure —$R_4$—O—$R_5$, where $R_4$ is independently an alkylene radical of 1 to 5 carbon atoms, and $R_5$ is independently an alkyl radical of 1 to 5 carbon atoms.

Preferred hexahydrotriazines according to formula I include compounds in which $R_1$, $R_2$, and $R_3$ are the same and are either alkyl or hydroxyalkyl. More preferably they are ethyl or hydroxyethyl. Particularly preferred compounds are hexahydro-1,3,5-tris(2-hydroxyethyl)-s-triazine and hexahydro-1,3,5-triethyl-s-triazine.

Preferably, the DBNPA to hexahydrotriazine weight ratio in the third embodiment of the invention is between about 100:1 to 1:100, more preferably 50:1 to 1:50, and even more preferably 20:1 to 1:20. In a particularly preferred embodiment, the DBNPA to hexahydrotriazine weight ratio is between about 8:1 to 1.9.

In a further embodiment, the microorganism is aerobic. Under this embodiment, a preferred DBNPA to hexahydrotriazine weight ratio is about 8:1.

In a yet further embodiment, the microorganism is anaerobic. Under this embodiment, the DBNPA to hexahydrotriazine weight ratio is preferably between about 1:1 to 1:9.

Hexahydrotriazines according to formula I are commercially available and/or can be readily prepared by those skilled in the art using well known techniques (e.g. as described in U.S. Pat. Nos. 3,981,998, 4,978,512, and/or 5,347,007).

The compositions of the invention are useful for controlling microorganism growth in a variety of aqueous and water containing systems. Examples of such systems include, but are not limited to process water and aqueous systems present in oil and gas operations, cooling water, boiler water, pulp and paper mill water, other industrial process water, ballast water, wastewater, metalworking fluids, latex, paint, coatings, adhesives, inks, tape joint compounds, personal care and household products, aqueous emulsions, inks, pigment dispersions, and textile fluids. In addition, the blends may be employed in other areas where DBNPA is used as a biocide and longer-lasting microbial protection is desired.

Preferred aqueous or water containing systems are those present in oil and gas operations. Examples of aqueous or water-containing systems within oil and gas operations include, for instance, injection and produced water, source water for waterflooding and hydraulic fracturing such as pond water and holding tank water, functional fluids such as drilling muds, completion or workover fluids, hydrotest fluids, stimulation fluids, packer fluids, and fracturing fluids, oil and gas wells, separation, storage, and transportation systems, oil and gas pipelines, oil and gas vessels, or fuel.

A person of ordinary skill in the art can readily determine, without undue experimentation, the concentration of the composition that should be used in any particular application. By way of illustration, a suitable actives concentration (total for both DBNPA and the second biocide) is typically between 1 and 5000 ppm, preferably between 5 and 1000 ppm, based on the total weight of the aqueous or water containing system including the biocides. In some embodiments for oil and gas applications, it is preferred that active concentrations of the composition range from about 5 to about 300 ppm for top side treatment, and from about 30 to about 500 ppm for downhole treatment.

The components of the inventive compositions can be added to the aqueous or water containing system separately, or preblended prior to addition. A person of ordinary skill in the art can easily determine the appropriate method of addition. The composition can be used in the system with other additives such as, but not limited to, surfactants, ionic/nonionic polymers and scale and corrosion inhibitors, oxygen scavengers, and/or additional biocides.

"Alkyl," as used in this specification, encompasses straight and branched chain aliphatic groups. Preferred alkyl groups include, without limitation, methyl, ethyl, propyl, isopropyl, butyl, isobutyl, sec-butyl, tert-butyl, and pentyl.

By "hydroxyalkyl" is meant an alkyl group as defined herein above that is substituted with a hydroxyl group. Preferred hydroxyalkyl groups include, without limitation, hydroxymethyl and hydroxyethyl.

By "alkylene" is meant an alkyl group as defined herein above that is positioned between and serves to connect two other chemical groups. Preferred alkylene groups include, without limitation, methylene, ethylene, propylene, and butylene.

The following examples are illustrative of the invention but are not intended to limit its scope. Unless otherwise indicated, ratios, percentages, parts, and the like used herein are by weight.

EXAMPLES

The synergy indexes reported in the following examples are calculated using the following equation:

Synergy Index = $C_a/C_A + C_b/C_B$ where $C_a$: Concentration of biocide A required to achieve a certain level or complete bacterial kill when used in combination;

$C_A$: Concentration of biocide A required to achieve a certain level or complete bacterial kill when used alone;

$C_b$: Concentration of biocide B required to achieve a certain level or complete bacterial kill when used in combination; and $C_B$: Concentration of biocide B required to achieve a certain level or complete bacterial kill when used alone.

A synergy index (SI) of 1 indicates additivity, a synergy index of less than 1 indicates synergy, and a synergy index greater than 1 indicates antagonism.

Various methods known to those skilled in the art can be used for evaluating biocidal efficacy. In the examples below, aliquots of the treated samples are removed at predetermined time points and the concentration required to achieve a certain level or complete bacterial kill is determined by culture-based methods including serial dilution. In some examples, the method is based or adapted (e.g., for high temperature testing or for the presence of sulfide) from the methodology described in international application PCT/US08/075,755, filed Sep. 10, 2008, which is incorporated herein by reference.

Example 1

Evaluation of DBNPA/CTAC, DBNPA/tris(hydroxymethyl)nitromethane (tris nitro), and DBNPA/hexahydro-1,3,5-tris(2-hydroxyethyl)-s-triazine (HHT) combinations against anaerobic bacteria Inside an anaerobic chamber, a deaerated sterile salt solution (3.1183 g of NaCl, 1.3082 mg of NaHCO3, 47.70 mg of KCl, 72.00 mg of CaCl2, 54.49 mg of MgSO4, 172.28 mg of Na2SO4, 43.92 mg of Na2CO3 in 1 L water) is contaminated with an oil field isolated anaerobic SRB consortium at final bacterial concentrations of $10^6$-$10^7$ CFU/mL. Aliquots of this contaminated water are then treated with biocide solution (single or in combination) at various concentrations. After the mixtures are incubated at 40° C. for 24 hour, the minimum biocide concentration to achieve complete bacteria kill (MBC) is determined Table 1 summarizes the results for DBNPA/CTAC combinations, Table 2 summarizes the results for DBNPA/tris nitro, and Table 3 summarizes the results for DBNPA/HHT combinations.

TABLE 1

Biocidal efficacy of DBNPA, CTAC, and DBNPA/CTAC combinations against anaerobic bacteria.

| DBNPA:CTAC ratio | Dosage required for complete bacterial reduction (ppm) | | Synergy Index |
|---|---|---|---|
| | DBNPA | CTAC | |
| 1:0 | 9.1 | 0.0 | |
| 9:1 | 6.9 | 0.8 | 0.77 |
| 3:1 | 6.8 | 2.3 | 0.78 |
| 1:1 | 6.5 | 6.5 | 0.79 |
| 1:3 | 5.6 | 16.9 | 0.81 |
| 1:9 | 5.3 | 47.7 | 1.12 |
| 0:1 | 0.0 | 87.5 | |

TABLE 2

Biocidal efficacy of DBNPA, tris nitro, and DBNPA/tris nitro combinations against anaerobic bacteria

| DBNPA:tris nitro ratio | Dosage required for complete bacterial reduction (ppm) | | Synergy Index |
|---|---|---|---|
| | DBNPA | tris nitro | |
| 1:0 | 8.9 | 0.0 | |
| 9:1 | 5.8 | 0.7 | 0.67 |
| 3:1 | 8.3 | 2.8 | 1.03 |
| 1:1 | 7.4 | 7.4 | 1.08 |
| 1:3 | 5.6 | 16.7 | 1.19 |
| 1:9 | 4.8 | 42.8 | 1.98 |
| 0:1 | 0.0 | 29.6 | |

TABLE 3

Biocidal efficacy of DBNPA, HHT, and DBNPA/HHT combinations against anaerobic bacteria

| DBNPA:HHT ratio | Dosage required for complete bacterial reduction (ppm) | | Synergy Index |
|---|---|---|---|
| | DBNPA | HHT | |
| 1:0 | 7.0 | 0.0 | |
| 9:1 | 6.9 | 0.8 | 1.00 |
| 3:1 | 6.8 | 2.3 | 1.00 |
| 1:1 | 6.5 | 6.5 | 0.98 |
| 1:3 | 5.6 | 16.9 | 0.95 |
| 1:9 | 4.1 | 36.7 | 0.90 |
| 0:1 | 0.0 | 113.8 | |

As shown in Tables 1-3, DBNPA in combination with CTAC, tris nitro, or HHT exhibits a synergistic effect against anaerobic SRB at certain weight ratios. Lower dosages can therefore be used for good bacterial control when the biocides are used in combination instead of separately.

Example 2

Evaluation of DBNPA/CTAC, DBNPA/tris(hydroxymethyl)nitromethane (tris nitro), and DBNPA/hexahydro-1,3,5-tris(2-hydroxyethyl)-s-triazine (HHT) combinations against aerobic bacteria A sterile NaCl solution (0.85%) is contaminated with *Psedomonas aeruginosa* ATCC 10145 and *Staphylococcus aureus* ATCC 6538 at a final bacterial concentration of ~$10^6$ CFU/ml. Aliquots of this contaminated water are then treated with biocide solution (single or in combination) at various concentrations. After the mixtures are incubated at 37° C. for 24 hour, the minimum biocide concentration to achieve complete bacteria kill (MBC) is determined Table 4 summarizes the results for DBNPA/CTAC combinations, Table 5 summarizes the results for DBNPA/tris nitro combinations, and Table 6 summarizes the results for DBNPA/HHT combinations.

TABLE 4

Biocidal efficacy of DBNPA, CTAC, and DBNPA/CTAC combinations against aerobic bacteria.

| DBNPA:CTAC ratio | Dosage required for complete bacterial reduction (ppm) | | Synergy Index |
|---|---|---|---|
| | DBNPA | CTAC | |
| 1:0 | 8.9 | 0.0 | |
| 9.8:1 | 6.8 | 0.7 | <0.77 |
| 3.9:1 | 6.8 | 1.7 | <0.78 |
| 1.3:1 | 8.9 | 6.8 | <1.04 |
| 1:2.2 | 8.9 | 19.5 | <1.12 |
| 1:6.2 | 6.8 | 42.6 | <1.04 |
| 0:1 | 0.0 | >159 | |

TABLE 5

Biocidal efficacy of DBNPA, tris nitro, and DBNPA/tris nitro combinations against aerobic bacteria

| DBNPA:tris nitro ratio | Dosage required for complete bacterial reduction (ppm) | | Synergy Index |
|---|---|---|---|
| | DBNPA | tris nitro | |
| 1:0 | 9.9 | 0.0 | |
| 7.6:1 | 9.9 | 1.3 | 1.01 |
| 2.9:1 | 9.9 | 3.3 | 1.03 |
| 1:1 | 9.9 | 9.9 | 1.09 |
| 1:2.9 | 4.5 | 12.9 | 0.58 |
| 1:8.2 | 3.5 | 28.1 | 0.62 |
| 0:1 | 0.0 | 104.6 | |

TABLE 6

Biocidal efficacy of DBNPA, HHT, and DBNPA/HHT combinations against aerobic bacteria

| DBNPA:HHT ratio | Dosage required for complete bacterial reduction (ppm) | | Synergy Index |
|---|---|---|---|
| | DBNPA | HHT | |
| 1:0 | 8.9 | 0.0 | |
| 8.2:1 | 6.8 | 0.9 | 0.78 |
| 2.9:1 | 8.9 | 3.0 | 1.03 |
| 1:1 | 8.9 | 8.9 | 1.09 |
| 1:2.9 | 8.9 | 25.4 | 1.27 |
| 1:8.2 | 6.8 | 55.5 | 1.36 |
| 0:1 | 0.0 | 94.2 | |

As shown in Tables 4-6, DBNPA in combination with CTAC, tris nitro, or HHT exhibits a synergistic effect against aerobic bacteria at certain weight ratios. Lower dosages can therefore be used for good bacterial control when the biocides are used in combination instead of separately.

Example 3

Evaluation of DBNPA, CTAC, and DBNPA/CTAC Combinations Against Aerobic Bacteria in a Re-Challenge Test DBNPA and CTAC is added to a sterile solution of synthetic surface water (CaCl2 0.2203 g, MgSO4 0.1847 g, NaHCO3 0.1848 g, DI water 1 L) both alone and in various combinations. An initial inoculum of a mixed bacteria consortium (*Pseudomonas aeruginosa* ATCC 10145, *Pseudomonas aeruginosa* ATCC 15422, *Enterobacter aerogenes* ATCC 13048, *Escherichia coli* ATCC 11229, *Klebsiella pneumoniae* ATCC 8308, *Staphylococcus aureus* ATCC 6538, *Salmonella choleraesuis* ATCC 10708) is added to each biocidal solution at a final concentration of $5 \times 10^6$ CFU/mL. After 2, 6 and 13 days, the biocidal solutions are re-challenged with the same bacteria consortium to a final concentration of $5 \times 10^4$ CFU/mL of additional bacteria. All treatments are incubated at ambient temperatures. The results are shown in Table 7 which reports the biocide concentrations required to achieve a $\geq 4 \log_{10}$ kill reduction in microorganisms.

TABLE 7

Biocidal efficacy of DBNPA, CTAC, and DBNPA/CTAC combinations against aerobic bacteria in a re-challenge test.

| Days After Initial Inoculation | DBNPA:CTAC ratio | Dose required for ≥4 $\log_{10}$ bacteria reduction (ppm) | | Synergy Index |
|---|---|---|---|---|
| | | DBNPA | CTAC | |
| Day 3 | 1:0 | >167 | | |
| | 1:34.1 | 15 | 500 | 0.75 |
| | 1:22.7 | 15 | 333 | 0.53 |
| | 1:6.7 | 22 | 148 | 0.33 |
| | 1:4.5 | 22 | 99 | 0.26 |
| | 1:3 | 33 | 99 | 0.33 |
| | 1.1:1 | 111 | 99 | 0.80 |
| | 0:1 | | >750 | |
| Day 20 | 1:0 | >250 | | |
| | 1:34.1 | 15 | 500 | 0.73 |
| | 1:22.7 | 15 | 333 | 0.50 |
| | 1:10.1 | 22 | 222 | 0.38 |
| | 1:6.7 | 22 | 148 | 0.29 |
| | 1:4.5 | 22 | 99 | 0.22 |
| | 1:3 | 33 | 99 | 0.26 |
| | 1.1:1 | 111 | 99 | 0.58 |
| | 0:1 | | >750 | |

As can be seen in Table 7, DBNPA in combination with CTAC is synergistic against multiple challenges of aerobic bacteria and over extended time periods.

Example 4

Evaluation of DBNPA, CTAC, and DBNPA/CTAC Combinations Against Anaerobic Bacteria Under Sulfide-Rich and Multiple Challenge Conditions Inside an anaerobic chamber, biocide solutions of DBNPA, CTAC, and DBNPA/CTAC combinations at various concentrations are prepared in a salt solution (3.1183 g of NaCl, 1.3082 mg of NaHCO3, 47.70 mg of KCl, 72.00 mg of CaCl2, 54.49 mg of MgSO4, 172.28 mg of Na2SO4, 43.92 mg of Na2CO3 in 1 L water). Aliquots of the biocide solutions are then inoculated with an oil field isolated anaerobic SRB consortium at final bacterial concentrations of ~$10^7$ CFU/mL. The mixtures are incubated at room temperature and challenged daily with the SRB consortium ($10^4$ to $10^5$ CFU/mL) and 10 ppm sulfide ion. The viable bacteria left in the mixtures is determined at different incubation times up to 7 days, using a serial dilution method. Bacterial log reduction is then calculated. The biocidal efficacy is determined by selecting the lowest biocide concentration required to achieve at least a 99.9% bacterial reduction for all three of the following time points: 2 hour, 1 day, and 7 days. Synergy index is then calculated. The results are shown in Table 8.

TABLE 8

Biocidal efficacy of DBNPA, CTAC, and DBNPA/CTAC combinations against anaerobic bacteria under sulfide-rich and re-challenge conditions.

| DBNPA:CTAC ratio | Lowest biocide concentration required for ≥99.9% bacterial reduction for 2 h, 1 day, and 7 days (ppm) | | Synergy Index |
|---|---|---|---|
| | DBNPA | CTAC | |
| 1:0 | 60.0 | 0.0 | |
| 2:1 | 30.0 | 15.0 | <0.54 |
| 1:1 | 15.0 | 15.0 | <0.29 |
| 1:2 | 7.5 | 15.0 | <0.17 |
| 1:4 | 7.5 | 30.0 | <0.21 |
| 1:8 | 7.5 | 60.0 | <0.29 |
| 0:1 | 0.0 | >360.0 | |

As can be seen in Table 8, DBNPA in combination with CTAC is synergistic against multiple challenges of anaerobic bacteria and sulfide ion over extended time periods.

Example 5

Evaluation of DBNPA, CTAC, and DBNPA/CTAC Combinations Against Anaerobic Bacteria Under High Temperature, Sulfide-Rich, and Re-Challenge Conditions Inside an anaerobic chamber, biocide solutions of DBNPA, CTAC, and DBNPA/CTAC combinations at various concentrations are prepared in a salt solution (3.1183 g of NaCl, 1.3082 mg of NaHCO3, 47.70 mg of KCl, 72.00 mg of CaCl2, 54.49 mg of MgSO4, 172.28 mg of Na2SO4, 43.92 mg of Na2CO3 in 1 L water). Aliquots of the biocide solutions are then challenged with $10^4$ to $10^5$ CFU/mL of an oil field isolated anaerobic SRB consortium 10 ppm sulfide ion and then incubated at 80° C. under anaerobic conditions for 7 days. During the incubation, the mixtures are challenged daily with $10^4$-$10^5$ CFU/mL of the oilfield SRB consortium and 10 ppm sulfide ion. After heating at 80 C for 2 hours, biocidal efficacy is evaluated against the field SRB consortium at 40° C. for 2 h. The same samples, after heating for 1 day to 7 days at 80 C, are evaluated against the field SRB consortium at 40 C for 24 h. The biocidal efficacy is determined by selecting the lowest biocide concentration required to achieve at least a 99.9% bacterial reduction for all three of the following time points: 2 hour, 1 day, and 7 day. The results are shown in Table 9.

TABLE 9

Biocidal efficacy of DBNPA, CTAC, and DBNPA/CTAC combinations against anaerobic bacteria under high temperature, sulfide-rich, and re-challenge conditions.

| DBNPA:CTAC ratio | Lowest biocide concentration required for ≥99.9% bacterial reduction for 2 h, 1 day, and 7 days (ppm) | | Synergy Index |
|---|---|---|---|
| | DBNPA | CTAC | |
| 1:0 | >120 | 0 | |
| 2:1 | 120 | 60 | <1.33 |
| 1:1 | 60 | 60 | <0.83 |
| 1:2 | 60.0 | 120.0 | <1.17 |
| 1:4 | 30.0 | 120.0 | <0.92 |
| 1:8 | 30 | 240 | <1.58 |
| 0:1 | 0 | 180 | |

As can be seen in Table 9, DBNPA in combination with CTAC at certain weight ratios is synergistic against multiple challenges of anaerobic bacteria in the presence of sulfide ion under high temperature conditions and over extended time periods.

Example 6

Evaluation of Ternary DBNPA, CTAC, and Bronopol Combination

DBNPA, bronopol, and CTAC are added to a sterile solution of synthetic surface water ($CaCl_2$ 0.2203 g, $MgSO_4$ 0.1847 g, $NaHCO_3$ 0.1848 g, deionized water 1 L) both alone and in various combinations. An initial inoculum of a mixed bacteria consortium (*Pseudomonas aeruginosa* ATCC 10145, *Pseudomonas aeruginosa* ATCC 15422, *Enterobacter aerogenes* ATCC 13048, *Escherichia coli* ATCC 11229, *Klebsiella pneumoniae* ATCC 8308, *Staphylococcus aureus* ATCC 6538, *Salmonella choleraesuis* ATCC 10708) is added to each biocidal solution at a final concentration of $5 \times 10^6$ CFU/mL. After 2, 6 and 13 days, the biocidal solutions are re-challenged with the same bacteria consortium to a final concentration of $5 \times 10^4$ CFU/mL of additional bacteria. All treatments are incubated at ambient temperatures. The results are shown in Table 10 which reports the biocide concentrations required to achieve a ≥4 $\log_{10}$ kill reduction in microorganisms.

TABLE 10

| Days After Initial Inoculation | DBNPA:bnpd: CTAC ratio | Dose required for >4 $\log_{10}$ bacterial reduction vs. control | | | Synergy Index |
|---|---|---|---|---|---|
| | | DBNPA | bnpd | CTAC | |
| Day 3 | 1:0:0 | <12 | | | |
| | 0:1:0 | | 32 | | |
| | 0:0:1 | | | >750 | |
| | 1:3:16 | 4 | 12 | 64 | 0.51 |
| | 1:1:8 | 8 | 8 | 64 | 0.44 |
| | 1:1:4.7 | 12 | 12 | 56 | 0.61 |
| | 1:2:7 | 8 | 16 | 56 | 0.68 |
| | 1:5:14 | 4 | 20 | 56 | 0.75 |
| | 1:1:3 | 16 | 16 | 48 | 0.78 |
| | 1:3:6 | 8 | 24 | 48 | 0.92 |
| Day 27 | 1:0:0 | >75 | | | |
| | 0:1:0 | | >200 | | |
| | 0:0:1 | | | >750 | |
| | 1:3:16 | 11.4 | 34.2 | 182.4 | 0.57 |
| | 1:1:8 | 17.5 | 17.5 | 140 | 0.51 |
| | 1:1:4.7 | 26.25 | 26.25 | 122.5 | 0.64 |
| | 1:2:7 | 22.8 | 45.6 | 159.6 | 0.74 |
| | 1:5:14 | 11.4 | 57 | 159.6 | 0.65 |
| | 1:1:3 | 100 | 100 | 300 | ≤2.23 |
| | 1:3:6 | 38.5 | 115.5 | 231 | ≤1.40 |

Bnpd = bronopol

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:
1. A synergistic composition for controlling anaerobic microorganisms comprising:

2,2-dibromo-3-nitrilopropionamide and 1-(3-chloroallyl)-3,5,7-triaza-1-azoniaadamantane wherein the weight ratio of 2,2-dibromo-3-nitrilopropionamide to 1-(3-chloroallyl)-3,5,7-triaza-1-azoniaadamantane is from 9:1 to 1:3.

2. A composition according to claim 1 further comprising one or more surfactants, ionic/nonionic polymers and scale, corrosion inhibitors, oxygen scavengers or additional biocides.

3. A method for controlling microorganisms in an aqueous or water containing system, the method comprising treating the system with an effective amount of a composition according to claim 1.

4. A method according to claim 3 wherein the aqueous or water containing system is used or is present in oil and or gas production.

5. A method according to claim 4 wherein oil and gas production comprises injection and produced water, source water for waterflooding and hydraulic fracturing, pond water, holding tank water, functional fluids, drilling muds, completion and workover fluids, hydrotest fluids, stimulation fluids, packer fluids, fracturing fluids, oil and gas wells, separation, storage and transportation systems, oil and gas pipelines, oil and gas vessels, or fuel.

6. A method according to claim 3 wherein the aqueous or water containing system is cooling water, boiler water, pulp and paper mill water, other industrial process water, ballast water, wastewater, metalworking fluids, leather treatment fluids, paints and coatings, aqueous emulsions, latexes, adhesives, inks, pigment dispersions, personal care and household products, mineral slurries, caulks and adhesives, tape joint compounds, disinfectants, cleaners, or a system used therewith.

7. A synergistic composition for controlling aerobic microorganisms comprising:
2,2-dibromo-3-nitrilopropionamide; and 1-(3-chloroallyl)-3,5,7-triaza-1-azoniaadamantane wherein the weight ratio of 2,2-dibromo-3-nitrilopropionamide to 1-(3-chloroallyl)-3,5,7-triaza-1-azoniaadamantane is from 9.8:1 to 3.9:1.

8. A composition according to claim 7 further comprising one or more surfactants, ionic/nonionic polymers and scale, corrosion inhibitors, oxygen scavengers or additional biocides.

* * * * *